(12) United States Patent
Klipstein et al.

(10) Patent No.: US 7,758,204 B2
(45) Date of Patent: Jul. 20, 2010

(54) LED SPOTLIGHT

(75) Inventors: Donald L. Klipstein, Upper Darby, PA (US); Jack Brass, North York (CA); Robert Tod Whitfield, Toronto (CA)

(73) Assignee: Brasscorp Limited (CA)

( * ) Notice: Subject to any disclaimer, the term of this patent is extended or adjusted under 35 U.S.C. 154(b) by 318 days.

(21) Appl. No.: 11/627,913

(22) Filed: Jan. 26, 2007

(65) Prior Publication Data

US 2007/0253188 A1    Nov. 1, 2007

Related U.S. Application Data

(60) Provisional application No. 60/762,380, filed on Jan. 26, 2006, provisional application No. 60/764,695, filed on Feb. 2, 2006.

(51) Int. Cl.
*F21L 4/04*    (2006.01)

(52) U.S. Cl. .................... 362/202; 362/171; 362/178; 362/296.1; 362/800; 362/103; 362/105

(58) Field of Classification Search ......... 362/349, 362/347, 327, 296, 341, 514, 516, 518, 215, 362/297, 103, 105, 311.02, 311.06–311.1, 362/335, 800, 200
See application file for complete search history.

(56) References Cited

U.S. PATENT DOCUMENTS

| | | | |
|---|---|---|---|
| D215,751 S * | 10/1969 | Castellano | D26/38 |
| 3,808,434 A | 4/1974 | Gutbier | |
| 4,185,891 A | 1/1980 | Kaestner | |
| 4,826,269 A | 5/1989 | Streifer et al. | |
| 4,935,665 A | 6/1990 | Murata | |

(Continued)

FOREIGN PATENT DOCUMENTS

CA    2200364 C    5/1997

(Continued)

OTHER PUBLICATIONS

Edmund Optics Inc., Techspec Precision Aspheric Lenses, http://www.edmundoptics.com/onlinecatalog/DisplayProduct.cfm?productid=2686, Mar. 15, 2007, Barrington, NJ, USA.

(Continued)

*Primary Examiner*—Sandra L O'Shea
*Assistant Examiner*—Danielle Allen
(74) *Attorney, Agent, or Firm*—Katten Muchin Rosenman LLP

(57) ABSTRACT

An LED spotlight is made with at least one light emitting diode and a lens placed forward of the light emitting diode to collimate the light from the light emitting diode into a beam. The light emitting diode is preferably a type with a nominal power of at least 1 watt, requiring heatsinking, and having a nominal radiation pattern width of 100 degrees or more. The lens is preferably concavo-convex. The lens can have a thickness less than the distance between the rear surface of the lens and the light emitting diode. The LED spotlight can be mounted on headwear that would be worn on a person's head. The LED spotlight can be in the form of a flashlight. The LED spotlight can be in the form of an inspection lamp suitable for causing visible fluorescence of fluorescent materials, such as leaks of fluids that have suitable fluorescent dyes.

47 Claims, 5 Drawing Sheets

U.S. PATENT DOCUMENTS

| | | | |
|---|---|---|---|
| 4,963,798 | A | 10/1990 | McDermott |
| 5,092,331 | A | 3/1992 | Nakamuura et al. |
| 5,289,082 | A | 2/1994 | Komoto |
| D349,123 | S * | 7/1994 | Cooley et al. ............... D16/309 |
| 5,410,453 | A * | 4/1995 | Ruskouski .................... 362/20 |
| 5,749,830 | A | 5/1998 | Kaneko et al. |
| 5,757,557 | A | 5/1998 | Medvedev et al. |
| 5,785,404 | A | 7/1998 | Wiese |
| 5,806,961 | A | 9/1998 | Dalton et al. |
| 5,954,206 | A | 9/1999 | Mallon et al. |
| 5,975,712 | A | 11/1999 | Shiao |
| 5,984,861 | A | 11/1999 | Crowley |
| 6,095,661 | A | 8/2000 | Lebens et al. |
| 6,142,650 | A | 11/2000 | Brown et al. |
| D434,868 | S | 12/2000 | Trigiani |
| 6,165,384 | A | 12/2000 | Cooper et al. |
| 6,183,086 | B1 | 2/2001 | Neubert |
| 6,190,020 | B1 | 2/2001 | Hartley |
| 6,200,134 | B1 | 3/2001 | Kovac et al. |
| 6,250,771 | B1 | 6/2001 | Sharrah et al. |
| 6,305,818 | B1 | 10/2001 | Lebens et al. |
| 6,357,893 | B1 | 3/2002 | Belliveau |
| 6,402,347 | B1 | 6/2002 | Maas et al. |
| 6,468,077 | B1 | 10/2002 | Melikechi et al. |
| 6,485,160 | B1 | 11/2002 | Sommers et al. |
| 6,491,408 | B1 | 12/2002 | Cooper et al. |
| 6,511,203 | B1 | 1/2003 | Winther |
| D472,890 | S * | 4/2003 | Suzuki ....................... D14/223 |
| 6,590,220 | B1 | 7/2003 | Kalley et al. |
| 6,630,682 | B2 * | 10/2003 | Shanley et al. .......... 250/504 R |
| 6,637,923 | B2 | 10/2003 | Amano |
| 6,710,363 | B1 | 3/2004 | Trigiani |
| 6,805,476 | B2 | 10/2004 | Amano |
| 6,866,401 | B2 | 3/2005 | Sommers et al. |
| 6,940,704 | B2 * | 9/2005 | Stalions ....................... 361/241 |
| 7,029,150 | B2 | 4/2006 | Finch |
| 7,083,297 | B2 | 8/2006 | Matthews et al. |
| 7,153,004 | B2 | 12/2006 | Galli |
| 7,267,466 | B2 * | 9/2007 | Reiss ......................... 362/545 |
| 2002/0012564 | A1 * | 1/2002 | Chao .......................... 401/195 |
| 2002/0074559 | A1 * | 6/2002 | Dowling et al. ............... 257/99 |
| 2002/0191396 | A1 | 12/2002 | Reiff et al. |
| 2003/0007345 | A1 | 1/2003 | Cooper et al. |
| 2003/0007346 | A1 | 1/2003 | Cooper et al. |
| 2003/0098425 | A1 | 5/2003 | Sosinsky |
| 2003/0123254 | A1 * | 7/2003 | Brass et al. ................. 362/231 |
| 2003/0142489 | A1 | 7/2003 | Cooper et al. |
| 2003/0165065 | A1 * | 9/2003 | Roller et al. ................. 362/522 |
| 2003/0169600 | A1 | 9/2003 | Amano |
| 2004/0223342 | A1 | 11/2004 | Klipstein et al. |
| 2005/0122713 | A1 * | 6/2005 | Hutchins ..................... 362/205 |

FOREIGN PATENT DOCUMENTS

| | | | |
|---|---|---|---|
| CA | 2200365 | A1 | 5/1997 |
| CA | 2280398 | A1 | 4/2000 |
| CA | 2405802 | A1 | 10/2001 |
| DE | 2542220 | A1 | 3/1977 |
| DE | 299574 | A5 | 4/1992 |
| DE | 20021934 | U1 | 4/2001 |
| DE | 20110813 | U1 | 9/2001 |
| EP | 0 523 927 | A2 | 1/1993 |
| EP | 1059202 | A2 | 12/2000 |
| GB | 810256 | | 3/1959 |
| WO | WO 98/39636 | A1 | 9/1998 |
| WO | WO 99/35486 | A1 | 7/1999 |
| WO | WO 01/52605 | A2 | 7/2001 |
| WO | WO 01/81973 | A1 | 11/2001 |
| WO | WO 03/004929 | A1 | 1/2003 |
| WO | WO 03/004932 | A1 | 1/2003 |
| WO | WO 03/025458 | A1 | 3/2003 |

OTHER PUBLICATIONS

Edmund Optics Inc., Aspheric Condenser Lenses, http://www.edmundoptics.com/onlinecatalog/displayproduct.cfm?productID=2454, Mar. 15, 2007, Barrington, NJ, USA.

Johnson, Craig, LEDTronics Mini-FlashLED, LED Museum, http://ledmuseum.home.att.net/flashled.htm, Jul. 30, 2004, pp. 1-7, Seattle, WA, USA.

Johnson, Craig, LEDTronics FlashLED, The LED Museum, http://ledmuseum.home.att.net/tronics.htm, Jul. 30 2004, pp. 1-14, Seattle, WA, USA.

Ledtronics, Inc., Hi-Power FlashLED Flashlights, www.ledtronics.com,http://netdisty.net/ds/flt-3001/default.asp, date unknown, p. 1,Torrance, CA, USA.

Osram Sylvania, Preliminary data sheet for OS-WL01A, Feb. 25, 2000, pp. 1-4, Germany.

Johnson, Craig, LED Museum, http://ledmuseum.home.att.net/menutop.htm, printed Jul. 30, 2004, pp. 1-15, Seattle, WA, USA.

Author Unknown, Cool Blue, Product pages for Dorcy, http:// www.dorcy.com/led%20new.htm, Feb. 27, 2002, pp. 1-2, Country of publication unknown.

Author Unknown, Hi-power FlashLED Flashlights, Safety LED, http://secure.implex.net/NBAComputers/browse.cfm?CategoryID=8, Dec. 10, 2001, p. 1, Country of publication unknown.

Johnson, Craig, CentraL.E.D. Work Light, The Punishment Zone, The LED Museum, Mar. 5, 2007, Sacramento, USA, http://ledmuseum.candlepower.us/sixth/clwl.htm.

Sayer, Michael, et al. Measurement, Instrumentation and Experiment Design in Physics and Engineering, 2000, pp. 197-198, Prentice-Hall of India, New Delhi, India.

Koller, Lewis R., Ultraviolet Radiation, 2nd ed., Wiley Series in Pure and Applied Optics, 1965, pp. 158-181, John Wiley & Sons, Inc., NY, USA.

Johnson, Craig, The LED Museum—LEDs—Gallium Indium Nitrate Uv, . . . , http://ledmuseum.home.att.net/index2.htm, Jul. 30, 2004, pp. 1-3, Seattle, WA, USA.

PRIMALEC, Invictalux product brochure, http://www.primalec.co.uk/pdfs/invictalux.pdf, Mar. 3, 2003, Kent, UK.

Johnson, Craig, Infinity Task Light, The Punishment Zone, The LED Museum, http://ledmuseum.home.att.net/infl.htm, Jun. 24, 2002, Seattle, USA.

Johnson, Craig, Arc Flashlight, The LED Museum, http://home.att.net/~ledmuseum/arclight.htm, Nov. 14, 2006, Seattle, USA.

LED Lighting Fixtures Inc., LLF : LED Lighting Fixtures : The New Standard in Downlighting, Apr. 4, 2007, Morrisville, North Carolina, USA, http://www.ledlightingfixtures.com/.

Maxxeon Inc., Maxxeon WorkStar—Cordless Rechargeable LED Work Lights, Apr. 4, 2007, Cambridge ON, Canada, http://www.maxxeon.com/?gclid=CL2fsZKn-loCFRkeYAodPAt9nw.

May 10, 2010 Office Action for U.S. Appl. No. 12/458,018.

* cited by examiner

LED SPOTLIGHT

The present application claims priority under 35 U.S.C. §119(e) to U.S. Provisional Application No. 60/762,380, filed on Jan. 26, 2006, and to U.S. Provisional Application No. 60/764,695, filed on Feb. 2, 2006, the entire contents of each of which are hereby incorporated by reference herein.

BACKGROUND

1. Field of the Invention

The invention relates to spotlights. In particular, the invention relates to LED spotlights, including LED flashlights and LED inspection lamps.

2. Background Information

Spotlights, including, for example, those used as flashlights or worn as headwear and those used as inspection lamps for causing visible fluorescence of fluorescent materials such as leaks of fluids having leak detection dyes, have been in use for decades. Historically, these products have conventionally used incandescent lamps including halogen lamps, although some lamps used for detection of fluorescent materials have used high intensity discharge lamps, such as high pressure mercury vapor lamps.

Light Emitting Diodes (LEDs) are being used for spotlights. The recent advent of high efficiency LEDs of wattages from 1 to 5 watts and recent efficiency improvements of these LEDs has allowed production of LED flashlights, LED lamps to be worn on or as headwear, and LED inspection lamps for detection of fluorescent materials. LED inspection lamps are also being used for the detection of leaks of suitably dyed lubricants in refrigeration systems, such as air conditioning systems.

Improvements to or alternatives for LED spotlights are desirable.

SUMMARY OF THE INVENTION

In a first aspect, the invention provides an LED spotlight having a housing, at least one LED within the housing, means for the at least one LED to receive electrical power, and at least one lens within the housing. Each lens of the at least one lens is disposed forward of an associated LED of the at least one LED. Each lens has a width of about 15 to about 26 millimeters. Each lens collimates a majority of the light from its associated LED into a beam no more than about 10 degrees wide, and all collimation of light by each lens occurs through refraction.

Rays of light from each LED can be refracted towards an axis of its associated lens upon entering the lens through a rear surface of the lens, and can be further refracted towards the axis of the lens upon exiting a front surface of the lens.

The lens can have a rear surface that is more sharply curved in a concave manner towards its edge than towards its axis. Each LED can have an optical center that is located closer to its associated lens than a focal point of the lens. Each LED can have an optical center that is located at a focal point of its associated lens.

Each LED can have a nominal radiation pattern width of at least about 100 degrees. Each LED can have a nominal wattage of approximately 1 watt or more. Each LED can nominally have a lambertian radiation pattern.

Each LED can receive power from an external power source. The housing can be metal so as to dissipate heat from the LED. Each LED can be mounted to a heatsink plate that conducts heat from the LED to the metal housing.

The distance between each LED of the at least one LED and its associated lens can be less than the thickness of the associated lens. The distance between each LED and its associated lens can be less than the distance that would produce a focused beam.

Each lens can be concavo-convex.

The spotlight can be, for example, a flashlight. At least one LED in a flashlight spotlight can produce light suitable for causing visible fluorescence of fluorescent materials to be detected by use of the flashlight. The light produced by the at least one LED can have a peak wavelength near about 365 nanometers. The light produced by the at least one LED can have a peak wavelength near about 380 nanometers. The light produced by the at least one LED can have a peak wavelength of about 390 to about 410 nanometers. The light produced by the at least one LED can have a peak wavelength in the blue region of the visible spectrum. The light produced by the at least one LED can have a peak wavelength near about 450 nanometers. The light produced by the at least one LED can have a peak wavelength of about 455 to about 475 nanometers.

The LED spotlight can be in combination with headwear. The headwear can be in the shape of an eyeglass frame or the like. The LED spotlight can be integrated with the headwear. The LED spotlight can be mounted to the headwear. The LED spotlight can be detachably mounted to the headwear. For example, a spotlight and headwear combination can be suitable for use while performing medical or dental work for the like.

The thickness of each lens at a central axis of the lens can exceed the distance between a rear surface of the lens at the central axis of the lens and its associated LED. Half the thickness of each lens at a central axis of the lens can exceed the distance between a rear surface of the lens at the central axis of the lens and its associated LED. Half the diameter of each lens can exceed the distance between a rear surface of each lens at a central axis of the lens and its associated LED.

The distance between each LED and its associated lens can be less than the distance that would produce a focused beam. A concave rear surface of any concavo-convex lens can have a convex central portion and a concave outer portion about the central portion.

Each LED of the at least one LED can have a radiation pattern width of about 55 degrees.

In a second aspect, the invention provides an LED spotlight having a housing, at least one LED within the housing, means for the at least one LED to receive electrical power, and at least one lens within the housing. Each lens of the at least one lens is disposed forward of an associated LED of the at least one LED. Each lens collimates a majority of the light from its associated LED into a beam no more than about 10 degrees wide, and all collimation of light by each lens occurs through refraction. Each LED of the at least one LED has a radiation pattern width of at least about 100 degrees.

In a third aspect, the invention provides an LED spotlight having a housing, at least one LED within the housing, means for the at least one LED to receive electrical power, and at least one lens within the housing. Each lens of the at least one lens is disposed forward of an associated LED of the at least one LED. Each lens has a width of about 15 to about 26 millimeters. Each lens is concavo-convex. Each lens has its rear surface more sharply curved in a concave manner towards its edge than towards its axis. The distance between each lens and its associated LED is less than the thickness of the lens. Each lens collimates light from the lens into a beam that has a width of no more than about 10 degrees, and all collimation of light by each lens occurs through refraction.

In a fourth aspect, the invention provides an LED spotlight having a housing, at least one LED within the housing, means for the at least one LED to receive electrical power, and at least one lens within the housing. Each lens of the at least one lens is disposed forward of an associated LED of the at least one LED. Each lens collimates a majority of the light from its associated LED into a beam no more than about 10 degrees wide. All collimation of light by each lens occurs through refraction. Each LED of the at least one LED has a radiation pattern width of essentially 55 degrees. Each LED has a power rating of at least about 1 watt. Each LED produces light of wavelengths suitable for causing visible fluorescence of fluorescent materials.

Elements of one aspect of the invention can be used in, or form part of, other aspects. For example, elements of the first aspect can be used in the second, third and fourth aspects.

BRIEF DESCRIPTION OF THE DRAWINGS

Other objects and advantages of the present invention will become apparent to those skilled in the art upon reading the following detailed description of preferred embodiments, in conjunction with the accompanying drawings, wherein like reference numerals have been used to designate like elements, and wherein.

DETAILED DESCRIPTION OF THE PREFERRED EMBODIMENTS

Throughout the present specification, the acronym "LED" is used to mean "light emitting diode".

Figure 1:
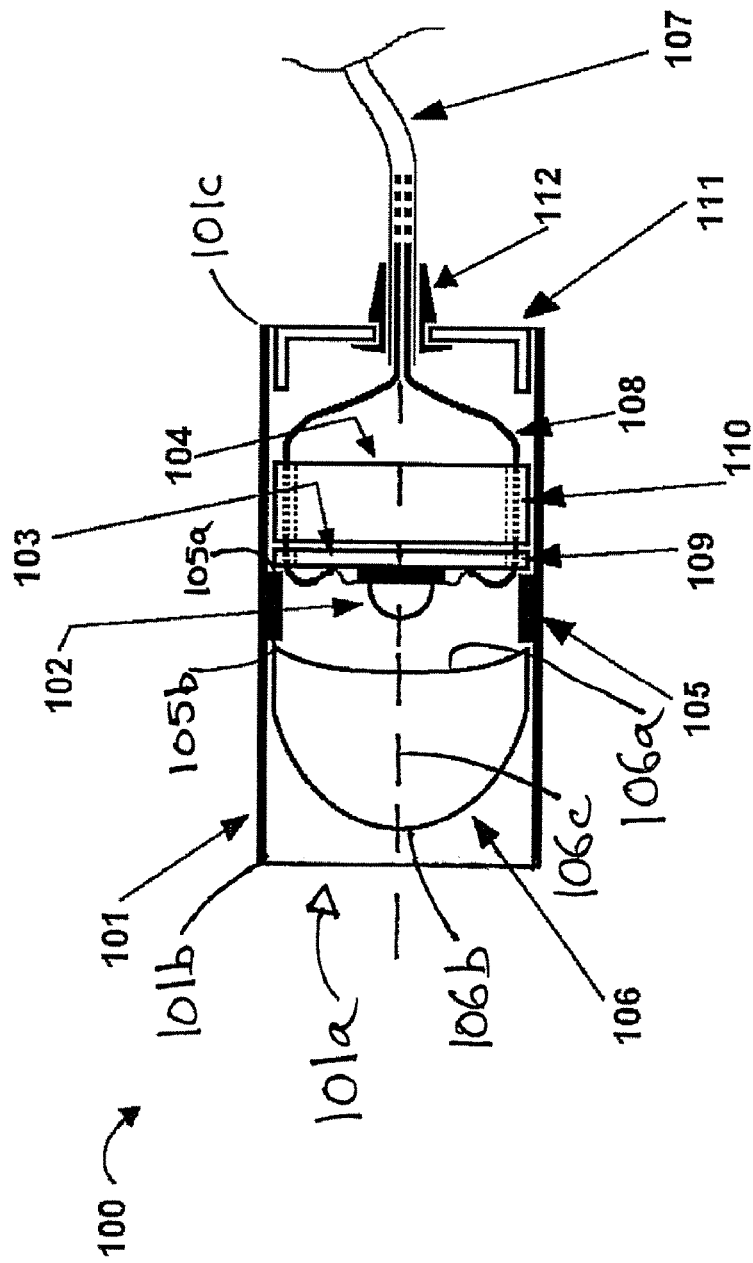
FIG. 1 is a cross sectional side view of a first exemplary embodiment of the present invention.

Referring to FIG. 1, an LED spotlight 100 includes a housing 101, an LED 102, and a lens 106. The lens 106 collimates light from the LED 102 into a beam no more than about 10 degrees wide. All or substantially all collimation by the lens 106 occurs through refraction.

The LED 102 is mounted onto a heatsink plate 103. The heatsink plate 103 can, for example, be made of metal core printed circuit board as shown in FIG. 1. The LED 102 can, for example, have a nominal wattage of at least 1 watt. The LED 102 can be supplied as including the heatsink plate 103. The LED 102 can, for example, be a Luxeon™ Star with lambertian radiation pattern, although other LEDs may be found suitable. Luxeon™ Star LEDs are provided by Philips Lumileds Lighting Company (sometimes referred to as Lumileds) of San Jose, Calif. The Lumileds Luxeon™ Star is an example of an LED 102 that is supplied including a heatsink plate 103. In applications that do not require as much light as can be provided by an LED 102 with a heatsink plate 103, an alternative LED without a heatsink plate 103 can be used. For example, such an LED can be a Lumileds Luxeon™ Emitter. This can allow a reduction in size of the overall diameter of the spotlight 100.

The housing 101 is tubular to receive the LED 102 and the lens 106. The housing 101 can be made of metal or the like so as to dissipate heat from the LED 102. Alternative shapes can be suitable for the housing 101, provided the housing 101 has an opening 101a at one end 101b through which light can emit from the lens 106, and the lens 106 and LED 102 are held in desired relation to one another when in use. This can be done by the housing 101 as shown. The housing 101 can be made of an alternative material, such as plastic or the like, if the LED 102 will not overheat. The housing 101 can be made up of numerous components to perform the functions described herein, one need not utilize a tubular housing as shown in the figures. Other configurations for the housing 101 will be evident to those skilled in art based on their common general knowledge and the principles described herein.

The housing 101 can be machined, particularly if it is made from metal. The housing 101 can be machined with a lathe such as a CNC lathe or the like. Other materials for, and methods of manufacturing, the housing 101 will be evident to those skilled in art based on their common general knowledge and the principles described herein.

The housing 101 includes a region of reduced inside diameter 105 providing stop surfaces 105a and 105b that the LED 102 and lens 106 are mounted against. The stop surfaces 105a, 105b provide a positive indication of the desired distance between the lens 106 and the LED 102 to accurately longitudinally align the lens 106 and the LED 102. The housing 101 also prevents stray light from exiting the housing 101 from around the lens 106.

The heatsink plate 103 of the LED 102 is held into place by a disc 104. The disc 104 can be attached to the housing 101 with glue. Alternatively, the disc 104 can be force-fitted into the housing 101. Further alternatively, the disc 104 and the interior of the housing 101 can be threaded so that the disc 104 can be screwed into place. Other means to mount the disc 104 will be evident to those skilled in art based on their common general knowledge and the principles described herein. Similarly, other means to mount the LED 102 will be evident to those skilled in art based on their common general knowledge and the principles described herein.

The lens 106 can be glued into the housing 101 or force fitted into the housing 101. Alternatively, the inside surface of the housing 101 can be threaded and a threaded ring, not shown, can hold the lens 106 into place against a region of the housing 101 where the inside diameter is reduced. Such mounting means can also be used to hold the heatsink plate 103 of the LED 102. Other means to mount the lens 106 will be evident to those skilled in art based on their common general knowledge and the principles described herein.

The lens 106 collimates light from the LED 102 into a beam. The lens 106 is concavo-convex in that rear surface 106a is concave and front surface 106b is convex. The front surface 106b is more sharply curved than the rear surface 106a. A concavo-convex shape can have benefits in allowing the rear surface 106a to permit transmission of additional light into the lens 106 from the LED 102. By placing the LED 102 sufficiently close to the lens 106, a majority of the light from the LED 102 will be collimated by the lens 106.

The concave rear surface 106a of the lens 106 can follow a curve defined by a polynomial function of a radius from axis 106c of the lens 106. The concave rear surface 106a can be, for example, spherical, ellipsoidal, or paraboloidal. The concave rear surface 106a of the lens 106 can have a shape that is a combination of an ellipsoid or spheroid and a shape generated by a polynomial function.

The front surface 106b of the lens 106 is typically aspheric. The shape of the front surface 106b of the lens 106 can be ellipsoidal, of a shape generated by a polynomial function of radius from the axis 106c of the lens 106, or a combination of a polynomial function shape and an ellipsoid or sphere.

The lens 106 is mounted close to the LED 102 and has a very highly convex front surface 106b in order to allow collimate light collected by the lens 106 from an LED 102 having a wide radiation pattern. Typically, the thickness of the lens 106 between the front surface 106b and the rear surface 106a along the axis 106c exceeds the distance between the lens 106 and the LED 102 along the axis 106c in order to collimate most of the light from an LED 102 having a nominal radiation pattern width of about 100 degrees or more. The distance between the LED 102 and the lens 106 can be half the thickness of the lens 106 or less. The distance between the LED 102 and the lens 106 can be less than half the diameter of the lens.

An LED 102 having a nominal radiation pattern width of about 100 degrees or more typically has a nominally lambertian radiation pattern, which ideally has an intensity at about 60 degrees from its axis equal to half the intensity at its axis and half its light within about 45 degrees of its axis. An LED 102 with a lambertian radiation pattern often has a nominal radiation pattern width of 120 degrees or close to 120 degrees. Other radiation pattern widths will also be suitable, for example, an XR-E™ LED by Cree, Inc. of Durham, N.C. is a suitable LED with optical requirements similar to those that have nominally lambertian radiation patterns and it has a rated radiation pattern width of 75 degrees. Other Xlamp™ LEDs by Cree, Inc. have a nominal radiation pattern width of 100 degrees and have been referred to as having a nominally lambertian radiation pattern.

The diameter of the lens 106 can be approximately the same as the overall width of the heatsink plate 103 of the LED 102 to capture and collimate maximal light, while not increasing the overall diameter of the spotlight 100. If the LED 102 is a Lumileds Luxeon™ Star, then this diameter would be approximately 21 millimeters. Other LEDs that typically require heatsinking, such as Cree, Inc.'s Xlamp™, can be purchased attached to circular heatsink plates approximately 20 millimeters in diameter.

Variations from the shown mounting arrangement can require that the lens 106 have a diameter slightly different from 20-21 millimeters in diameter. For example, the LED heatsink plate 103 can fit within a tubular region of the housing 101 that the lens 106 does not fit within, and so the lens diameter can be a few millimeters more than 20-21 millimeters in diameter. Alternatively, the lens 106 can fit within a tubular region of the housing 101 that the LED heatsink plate 103 does not fit within, and would typically necessitate the diameter of the lens 106 to be a few millimeters less than 20-21 millimeters. As a result, with typical wide angle LEDs 102 the diameter of the lens 106 with suitable capture to collimation characteristics would typically be about 15 to about 26 millimeters, although larger and smaller lenses 106 could be utilized for given applications.

A lens 106 that is 24 millimeters in diameter has been found to be able to produce a square beam that is approximately 5.5 degrees wide when used with a Lumileds Luxeon™ Star LED 102 having a nominally lambertian radiation pattern and a nominal wattage of 1 or 3 watts. Placing the lens 106 closer to the LED 102 than at a location that minimizes the width of a beam by achieving a focused beam (the "focal length") produces a beam that is wider, less square and more circular. The width of the beam when best-focused is determined by the effective size of the LED 102 light source and the focal length of the lens 106. Changing the focal length of the lens 106 while maintaining the efficiency of the lens 106 is, for example, accomplished by changing the size of the lens 106 while maintaining the shape of the lens 106. For the above Lumileds Luxeon™ Star example, achieving a beam of width about 3 degrees or less, or achieving a nearly circular beam of width near or less than 6 degrees, can be accomplished by having the diameter of the lens 106 greater than 26 millimeters. A lens 106 less than 15 millimeters in diameter and collimating most of the light from the Lumileds Luxeon™ Star LED 102 will typically produce either a square beam more than 6 degrees wide or a more circular beam that is wider. For many applications, it will be desirable to achieve a beam no more than 10 degrees wide in order to achieve high intensity of the beam. Achieving a beam of a given width with a lens 106 of smaller diameter using a Lumileds Luxeon™ Star LED 102 will typically result in a reduction in the amount of light collimated by the lens 106.

The lens 106 can be cast from a castable polymer such as acrylic, castable polycarbonate, or epoxy or the like. Alternatively, the lens 106 can be machined from a suitable material such as acrylic or thermoplastic polycarbonate and polished after machining. If the lens 106 is machined, it can be machined by means of a lathe such as a CNC lathe or the like. Further alternatively, the lens 106 can be injection molded if shape distortions that occur during cooling can be avoided or fixed. The lens 106 can alternatively be made of a non-polymer material such as glass or quartz, or made of a polymer by means other than casting, machining, or injection molding. Other methods of manufacturing a lens 106 will be evident to those skilled in art based on their common general knowledge and the principles described herein.

The LED spotlight 100 has a cable 107 with wires 108 to receive electrical power for the LED 102 from an external power source (not shown in FIG. 1, but see, for example, an alternative embodiment with pack 202 in FIG. 2 described later herein). A power source, such as, for example, a button cell battery or AA or AAA batteries, could be provided internal to the housing 101 if space permit and power requirements permit. Suitable current limiting means can be utilized to control, limit or regulate the magnitude of current flowing through the LED 102 as desirable to protect the LED 102 from excessive current that can otherwise flow. Such current limiting means would be preferably located at or within the external power source, where used, to minimize the size of the spotlight 100. The external power source can be, for example, a battery pack with a switch and the current limiting means can be, for example, a resistor or a current regulator. Other means to receive power for the LED 102 will be evident to those skilled in art based on their common general knowledge and the principles described herein. As an example, the LED 102 could be directly connected to a battery power source within the housing 101.

As shown, the LED heatsink plate 103 has notches 109 and the disc 104 has grooves 110 for the wires 108 to pass through. Alternatives to this arrangement are possible. For example, holes can be used instead of grooves. Clearance means for one wire can be eliminated by using the housing 101 as a conductor. The LED heatsink plate 103 can be non-circular, and this can allow wires 108 to pass around the LED heatsink plate 103. Grooves can be provided in the inner surface of the housing 101 to provide passage for wires 108. Wires 108 can be in the form of thin ribbons to reduce the need for the LED heatsink plate 103 and the disc 104 to have grooves, notches, or non-circular shape. Other means of providing power to the LED 102 will be evident to those skilled in art based on their common general knowledge and the principles described herein.

A rear housing piece 111 encloses end 101c of housing 101 opposing the end 101b. A cable strain relief 112 is shown as provided in the rear housing piece 111 to minimize fatigue damage to the wires 108 by flexing of them.

Figure 1A:
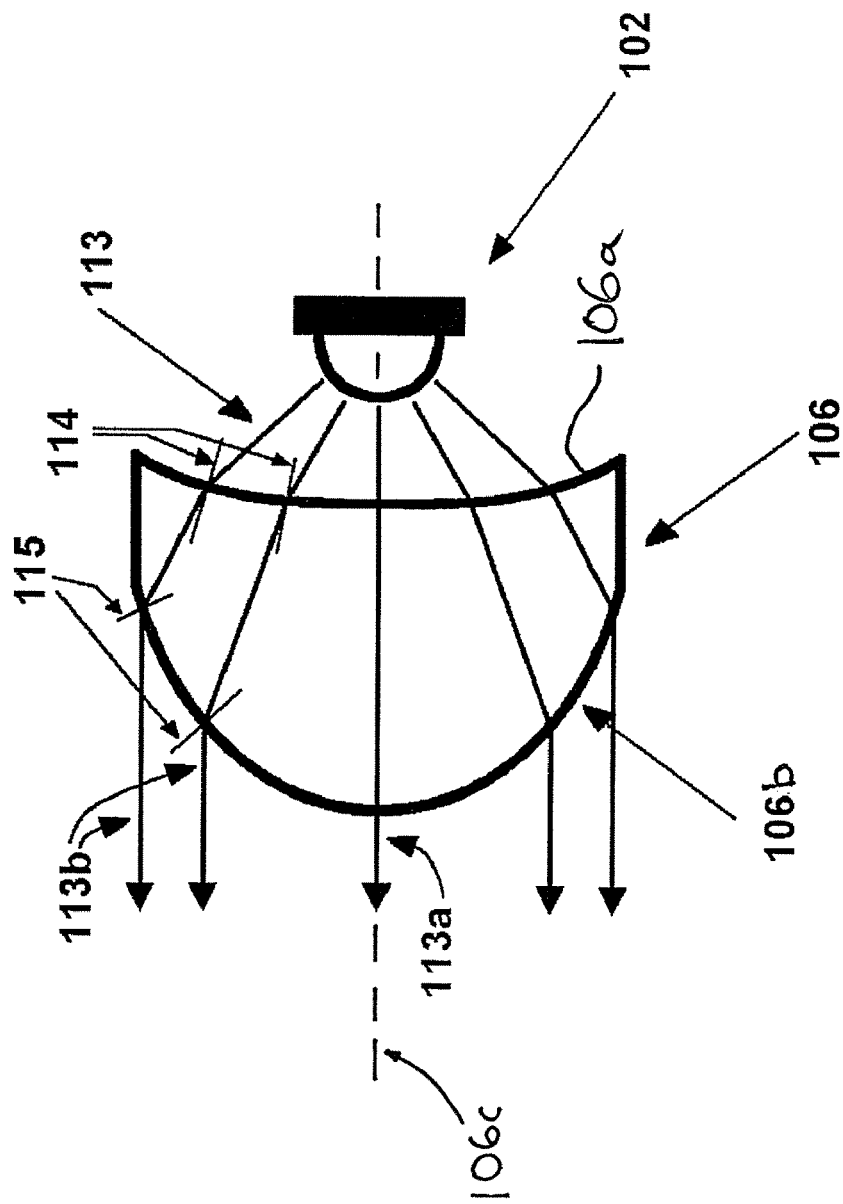
FIG. 1a is a ray trace diagram on a cross-sectional side view for a lens and LED combination used in the exemplary embodiment illustrated in FIG. 1.

Referring to FIG. 1a, light rays 113 produced by the LED 102 pass through the lens 106. The lens 106 comprises a convex front surface 106b and a rear surface 106a. The rear surface 106a is preferably concave. Either or both surfaces 106a, 106b can be aspheric. Preferably, the front surface 106b is approximately ellipsoidal. The front surface 106b can have alternative shapes as otherwise mentioned herein. For example, the front surface 106b can be spherical; however, light rays hitting an outer region of the front surface 106b can be almost parallel to it resulting in increased reflection loss of these rays. Also, any of such rays hitting the outer region of a spherical front surface 106b and not subject to total internal reflection can emerge from the front surface 106b converging towards the axis 106c of the lens 106 when rays emerging from a central region inside the outer region of a spherical front surface 106b would do so generally parallel to each other.

A ray 113a emitted by the LED 102 along the axis 106c of the lens 106 hits both lens surfaces 106a, 106b perpendicularly so it is not refracted, but neither is it collimated as it is on-axis. Off-axis rays 113b will be refracted since they will hit at least one lens surface 106a or 106b and preferably both 106a, 106b in a non-perpendicular manner.

The rear lens surface 106a is preferably concave with a curvature less sharp than an arc whose radius is equal to the distance between the rear lens surface 106a and the optical center (considered to be the location of the LED for optical purposes, and formed by an LED chip as discussed later below) of the LED 102. Normals 114 to the rear lens surface 106a exist at angles more parallel to the axis 106c of the lens 106 than the angles at which off-axis rays 113b arrive. As a result, the off-axis rays 113b are refracted towards the normals 114 to the rear lens surface 106a, and become slightly more parallel to the axis 106c of the lens 106 as a result.

If the rear lens surface 106a is excessively concave, then off-axis rays 113b would not be refracted towards the axis 106c of the lens 106, and the front lens surface 106b would have to do all of the collimation. However, if the rear lens surface 106a was not concave at all, then less light from the LED 102 would be collected by the rear lens surface 106a. Furthermore, if the rear lens surface 106a was not concave, off-axis rays 113b would hit the rear lens surface 106a less perpendicularly and experience more reflection.

The off-axis rays 113b, after being refracted by the rear lens surface 106a, pass through the lens 106 and then hit the front lens surface 106b. Normals 115 to the front lens surface 106b are shown. Off-axis rays 113b, upon exiting the lens 106 through its front surface 106b, are refracted away from the normals 115. If the optical center of the LED 102 is located at the focal point of the lens 106, then off-axis rays 113b from the optical center of the LED 102 will exit the lens 106 parallel to its axis, and a fully collimated beam will result. All collimation of light by the lens 106 occurs through refraction.

Figure 2:
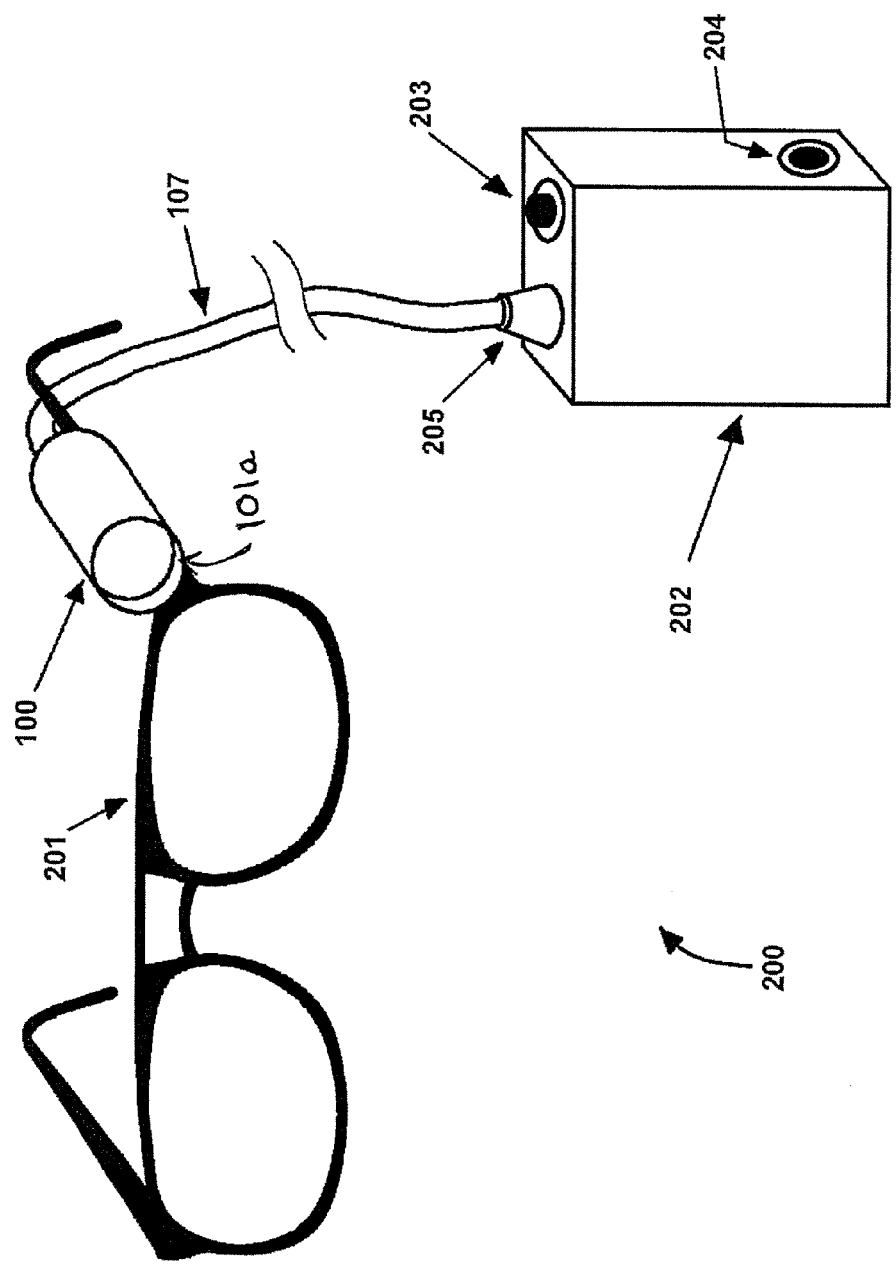
FIG. 2 is an external view of a system with the first exemplary embodiment of the present invention.

Referring generally to FIGS. 1 and 2, a specific detailed example of an implemented embodiment of the spotlight 100 will now be described. It is recognized that this is only one exemplary embodiment of many possible exemplary embodiments. The lens 106 was made of polymethylmethacrylate, an acrylic. This material was chosen because it is easier to machine for a custom batch than polycarbonate.

Polymethylmethacrylate has a refractive index of 1.50, while polycarbonate has a refractive index of 1.58. If the lens 106 is made of polycarbonate, then because of the higher refractive index the lens 106 can be thinner and have a less sharp curvature of its front surface 106b.

The lens 106 had a diameter of 23.8 mm. The diameter could be shaved down if some sacrifice in light is acceptable in order to make the spotlight 100 more compact with a clean and well-defined beam. Merely scaling the lens 106 down (as an alternative to shaving down its diameter) does not significantly decrease the percentage of light utilized, but does make the beam larger and typically less well defined.

The thickness along the axis was 15.1 mm. The front surface 106b curve was an ellipsoid, specifically an oblate spheroid, whose length (major axis dimension) is 1.28 times its diameter (minor axis dimension). The major axis dimension was 32 mm and the minor axis dimension was 25 mm. The major axis dimension was 2.119 times the thickness of the lens. The axis of the lens 106 is the major axis of the ellipsoid.

A 3-dimensional ellipsoid has 3 axes perpendicular to each other and passing through its center. One with a length and a diameter less than its length is an oblate spheroid, and has a major axis and two equal minor axes.

The diameter of the lens 106 cannot exceed the minor axis dimension of the ellipsoid that the front surface 106b is a portion of. With the implemented lens 106, the diameter was about 95% of the minor axis dimension.

More generally, the front curved surface 106b is preferably aspheric in the direction of an oblate spheroid or a paraboloid.

The rear surface 106a is concave, and in the implemented lens 106 was more sharply curved toward its edge and flatter towards its center at the lens axis 106c. This shape was used to allow for the combination of the lens rear surface 106a together with the lens front surface 106b to produce a collimated beam of approximately 5-6 degrees beam width. A different shape front surface 106b will allow a more spherical concave rear surface 106a.

The rear surface 106a for the implemented lens 106 is defined by a formula for how far rearward a point on the rear surface 106a is with respect to a plane perpendicular to the axis 106c and tangent to the rear surface 106a at its center which coincides with the axis 106c, as a function of radius from the axis 106c. This formula is for this particular implemented lens 106, as is used for purposes of illustration and not limitation. In the following Equation (1), R is radius from the axis 106c, and X is how far rearward from that plane the surface is at that R, with T being the thickness:

$$X = T*(0.2508*(R/T)^3 + 0.06886*(R/T)^4). \quad (1)$$

Equation (1) is a polynomial function with terms of order higher than two in order to generate a curve that is flatter in its center and curving more abruptly towards its edges than a paraboloidal surface or a spherical surface. If the concave surface is shallow compared to its diameter, then a paraboloidal surface has little difference from a spherical surface of same ratio of depth to diameter.

Other polynomial formulas with terms of order higher than two can be utilized. A suitable similar curve can be generated by a formula other than a polynomial one, such as, for example, a formula including an exponential term.

If desired a central portion of the rear surface 106a can be slightly convex as the curvature of the front surface 106b can be selected to sufficiently collimate light in this area. An outer region about the central portion could be concave as otherwise described herein.

With a thickness of 15.1 mm as provided above, the formula for rear surface distance X in millimeters from a plane tangent to its center as a function of radius R from axis 106c in millimeters is given by Equation (2):

$$X = 15.1*(0.2508 \times (R/15.1)^3 + 0.06886*(R/15.1)^4) \quad (2)$$

which simplifies to:

$$X = 0.0011*R^3 + 0.00002*R^4. \quad (3)$$

The focal length of a concavo-convex lens 106 is the same as that of a plano-convex one of the same thickness, refractive index and same front surface if the central region of the concave surface approximates being flat, which is the case if the concave surface is defined by a polynomial function with no terms of order equal to or less than 2.

The focal length in this case if the front surface 106b is an ellipsoid is the square of its minor axis divided by the product of twice its major axis and (refractive index minus 1). With a minor axis of 25 mm, a major axis of 32 mm, and a refractive index of 1.5, the focal length works out to 19.5 mm.

The focal length of the lens 106 is the distance between its focal point and its principal point. If a lens is plano-convex or concavo-convex with the central region of the concave surface essentially flat, and if the lens is being used to collimate light from a source behind the concave surface at the focal point into a beam comprising parallel rays, then the distance from the rear surface to the principal point is the thickness divided by the refractive index. In this case, this figure is (15.1 mm)/1.5, or 10.07 mm for distance between rear surface 106a and principal point. The focal point is rearward of the principal point by the focal length of 19.5 mm, or 9.4 mm rearward of the rear surface 106a at the central axis 106c. If the implemented lens 106 is scaled larger or smaller in size, then the distance between the rear surface and the focal point is similarly scaled, being 0.625 times the thickness of this lens.

If the center of the chip of the LED 102 (the LED light source, commonly referred to as the LED) is placed at the focal point of this particular lens 106 then rays up to approximately 46 degrees off axis 106c will be refracted by the rear surface 106a and the front surface 106b of this lens 106. If the convex front surface 106b ellipsoidal shape is continued to a depth rearward of the front of the lens 106 by half the ellipsoid's major axis, and the diameter is increased to the minor axis dimension of this ellipsoid, then rays emitted by the LED 102 up to approximately 57 degrees from the axis 106c will be refracted by the rear surface 106a and the front surface 106b. However, reflection losses at the front surface 106b will increase with rays emitted by the LED farther from its axis 106c.

If the chip of the LED 102 is located at the focal point of the lens 106, then the beam will comprise an image of the chip of the LED 102 and have the shape of the chip of the LED 102, which is typically square with 1-watt and 3-watt LEDs that are intended to mount onto a heatsink or metal core printed circuit board.

If the LED 102 is positioned for the beam to be best-focused at infinite or long distance, then the width of the beam will increase with distance forward of the LED 102 at a rate of width increase per unit distance equal to the ratio of effective LED 102 chip width to the focal length of the lens 106. In most 1-watt and 3-watt heatsinkable LEDs with a single chip, the chip size is approximately 1 millimeter, but effectively magnified to approximately 1.6 millimeters by the dome of a typical such LED of nominally lambertian radiation pattern. With the lens 106 having a focal length of 19.5 mm, the beam width increases per unit distance forward of the lens by 1.6/19.5, or 0.082 centimeter per centimeter, or a divergence angle of approximately 4.7 degrees if perfect focus is achieved at great distances. Any imperfection in focus is will typically increase the divergence rate.

A headwear-mounted spotlight 100 can be selected, for example, to illuminate an area approximately 5 centimeters wide at 25-30 cm, and slightly wider, such as 7 centimeters, at a somewhat longer distance such as 40-45 centimeters. In this example, the beam is initially 2.38 centimeters in diameter and diverges at a rate of 0.082 centimeter per centimeter of distance. At 25 centimeters, its width would be approximately 4.4 centimeters. At 45 centimeters, its width would be approximately 6.1 centimeters. A slightly more divergent beam approximately 5.5 centimeters wide at 25 centimeters forward of the lens and 7.8 centimeters wide at 45 centimeters forward of the lens 106 has also be found suitable and achieved by placing the chip of the LED 102 forward of the focal point by approximately 1-1.5 millimeters.

In some instances, it can be desirable to position the chip of the LED 102 slightly closer to the rear surface 106a of the lens 106 than the focal point of the lens 106. Although the beam becomes less focused and diverges at a greater rate, more light is collected and the beam is less square. As an example, the LED 102 chip can be positioned forward of the focal point by about or less than 10% of the thickness of the lens 106 for optimal results. A suitable LED 102 chip position improving on the focal point for the reasons described previously can be anywhere between the focal point of the lens and forward of the focal point by up to approximately 20% of the thickness of the lens 106 or up to approximately 15% of the focal length of the lens 106.

Referring to FIG. 2, an LED headlamp system 200 has the LED spotlight 100 and headwear 201 to wear on one's head and to which the LED spotlight 100 is mounted. The headwear 201 can be an eyeglass frame 201, but other forms of headwear 201 can be utilized, for example, a headband, a hardhat or a bicycle helmet or the like. The housing 101 can be integrated with the headwear 201. Other means of mounting the lens 106 and LED 102 with headwear 201 will be evident to those skilled in art based on their common general knowledge and the principles described herein.

The LED spotlight 100 can either be permanently attached to the headwear 201 or can be detachable. The means to mount the LED spotlight 100 to headwear 201 can, for example, include a hook and loop fastening system, a magnet, a clip or a strap or the like. Other means of means of mounting the spotlight 100 to headwear 201 will be evident to those skilled in art based on their common general knowledge and the principles described herein.

The LED spotlight 100 receives power from a battery pack 202 through a cable 107. Batteries (not shown) in the battery pack 202 may or may not be rechargeable. If the batteries are rechargeable, they can be, for example, nickel cadmium, nickel metal hydride, lead acid, or alternative rechargeable type such as lithium ion or lithium polymer. Other suitable batteries will be evident to those skilled in art based on their common general knowledge and the principles described herein.

The battery pack 202 can have a switch 203, a charging jack 204 and a cable strain relief 205.

The battery pack 202 can also include charging circuitry. The battery pack 202 can also include circuitry, for example, to protect the batteries from short circuits, overcharging, overdischarge or excessively unequal charge or discharge.

The LED headlamp system 200 can benefit from suitable means (not shown) to regulate or limit current flowing through the LED 102 in the LED spotlight 100. Such current regulating or limiting means can be a resistor, a linear current regulator, a switching current regulator, or an alternative type such as a boost converter that has current limiting or power regulating properties. The current regulating or limiting means is preferably located within the battery pack 202. Other current regulating or limiting means will be evident to those skilled in art based on their common general knowledge and the principles described herein.

The battery pack 202 can be sized to fit in one's pocket while the LED spotlight 100 is operating. Other shapes, dimensions and configurations of battery pack 202 will be evident to those skilled in art based on their common general knowledge and the principles described herein.

The LED headlamp system 200 can, for example, find applications during the performance of medical or dental examinations or other like procedures.

Figure 3:
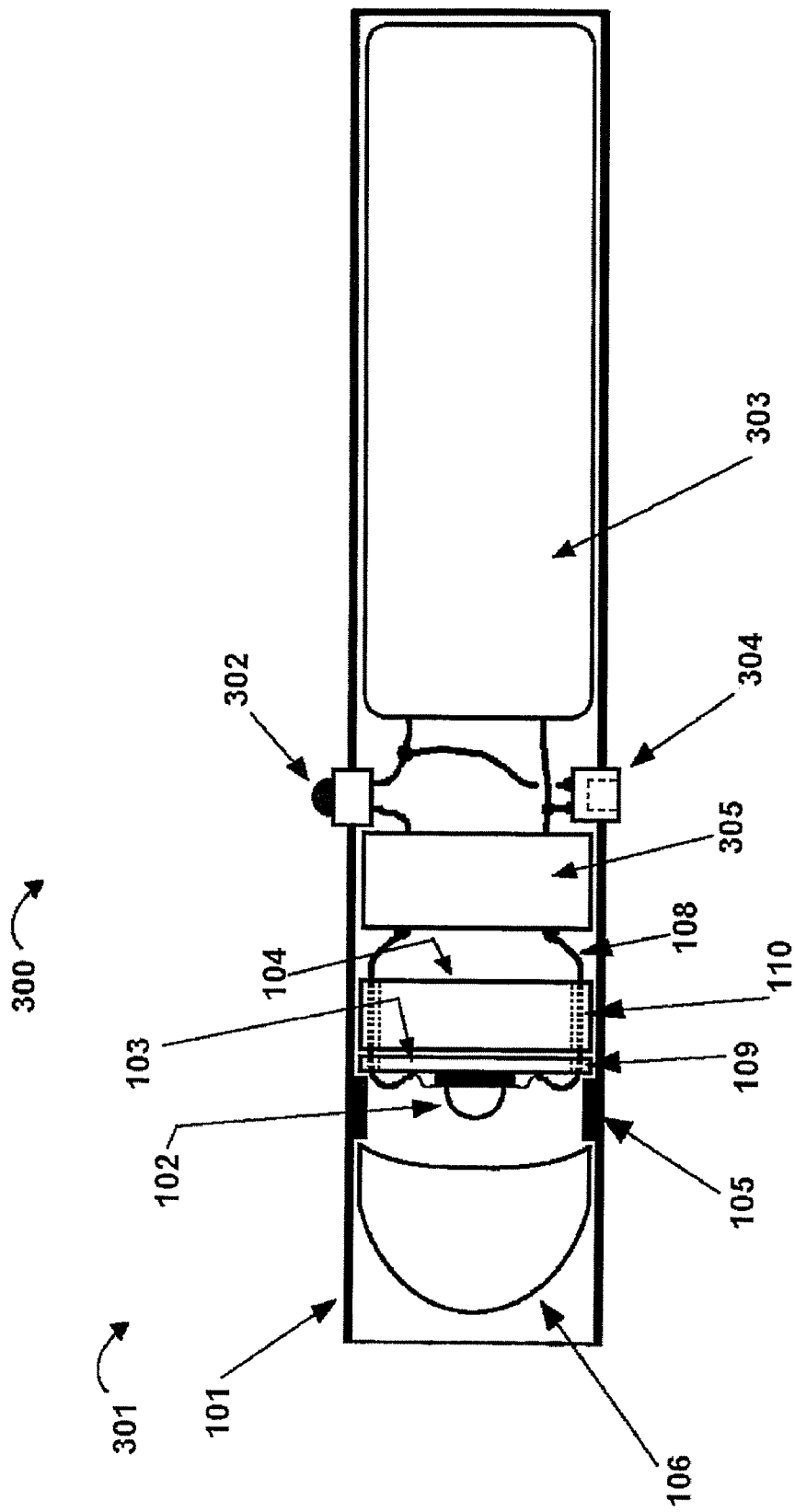
FIG. 3 is a cross sectional side view of a second exemplary embodiment of the present invention.

Referring to FIG. 3, an LED flashlight 300 includes a head section 301 similar to the LED spotlight 100 of FIG. 1 comprising LED 102, LED heatsink plate 103, disc 104, thick region 105 of the housing 101 used for mounting the LED 102, and lens 106. Like the arrangement of the LED spotlight 100 of FIG. 1, the LED heatsink plate 103 and the disc 104 are shown with grooves 109 and 110, respectively, to accommodate the wires 108. The LED flashlight 300 also includes a switch 302, a battery 303, a charging jack 304, and a circuit 305 as desired for controlling operation of the flashlight, such as the circuitry described above for charging the battery 303 or controlling current to the LED 102. The circuit 305 can, for example, be a current regulator or a boost converter. A resistor can, for example, be used for the circuit 305.

An inspection flashlight 300 suitable for detection of fluorescent materials can be achieved by utilizing an LED 102 in the LED flashlight 300 that produces suitable light for causing visible fluorescence of fluorescent materials. For example, the LED 102 could be one that produces blue, violet and/or ultraviolet light. The LED 102 can have a peak wavelength of approximately 365 nanometers in order to optimize fluorescence of materials that are optimized or selected for fluorescence from the 365-366 nanometer emission of mercury. The LED 102 can be a type with a peak wavelength of approximately 380 nanometers, since the cost of such an LED is less than that of a 365 nanometer one of similar power. Such an LED 102 can be an NCCU033 provided by Nichia America Corporation of Detroit, Mich. The LED 102 can have a peak wavelength in or near the 390-415 nanometer range, since such wavelengths are slightly visible and a slightly visible beam has been found advantageous in drawing attention to the area being irradiated without overwhelming fluorescence of materials to be detected. Such an LED 102 can be the Cree, Inc. XL7090UVV. The LED 102 can have a peak wavelength near 450 nanometers, since such a wavelength excites both perylene and naphthalimide that are used as leak detection dyes. The LED 102 can have a peak wavelength of about 455 to about 475 nanometers, since availability of LEDs of such a wavelength can be better and their cost can be lower than that of suitable LEDs with a peak wavelength near 450 nanometers. The LED 102 can have a peak wavelength near 530 nanometers in order to cause fluorescence of rhodamine 6G.

The LED 102 can alternatively be a type with nominal wattage at least 1 watt and with a radiation pattern narrower than a lambertian LED, such as Nichia's NCCU001 which has a peak wavelength of 380 nanometers and a nominal radiation pattern width of 55 degrees. A lens 106 of shape more conventional than that shown can be used with such an LED. Such a more conventional shape lens would typically be a biconvex, plano-convex or concavo-convex lens having a thickness near or less than half its diameter. Such a more conventional shape lens 106 may or may not have any curved surfaces being aspheric.

An LED inspection flashlight 300 can be used for detecting leaks of fluids containing suitable fluorescent dyes. An LED inspection flashlight 300 can be used for forensic applications such as detection of body fluids, as well as other suitable uses.

An LED inspection flashlight 300 can include a filter, for example, for the purpose of minimizing light of wavelengths similar to wavelengths produced by fluorescent materials to be detected with such an inspection flashlight 300. An LED inspection flashlight 300 or other form of the LED flashlight 300 can include a diffuser, for example, to smooth out irregularities in the beam. Such beam irregularities can result from features in or on or near a semiconductor chip of the LED 102, such as wirebonds and contacts, not shown.

Figure 4:
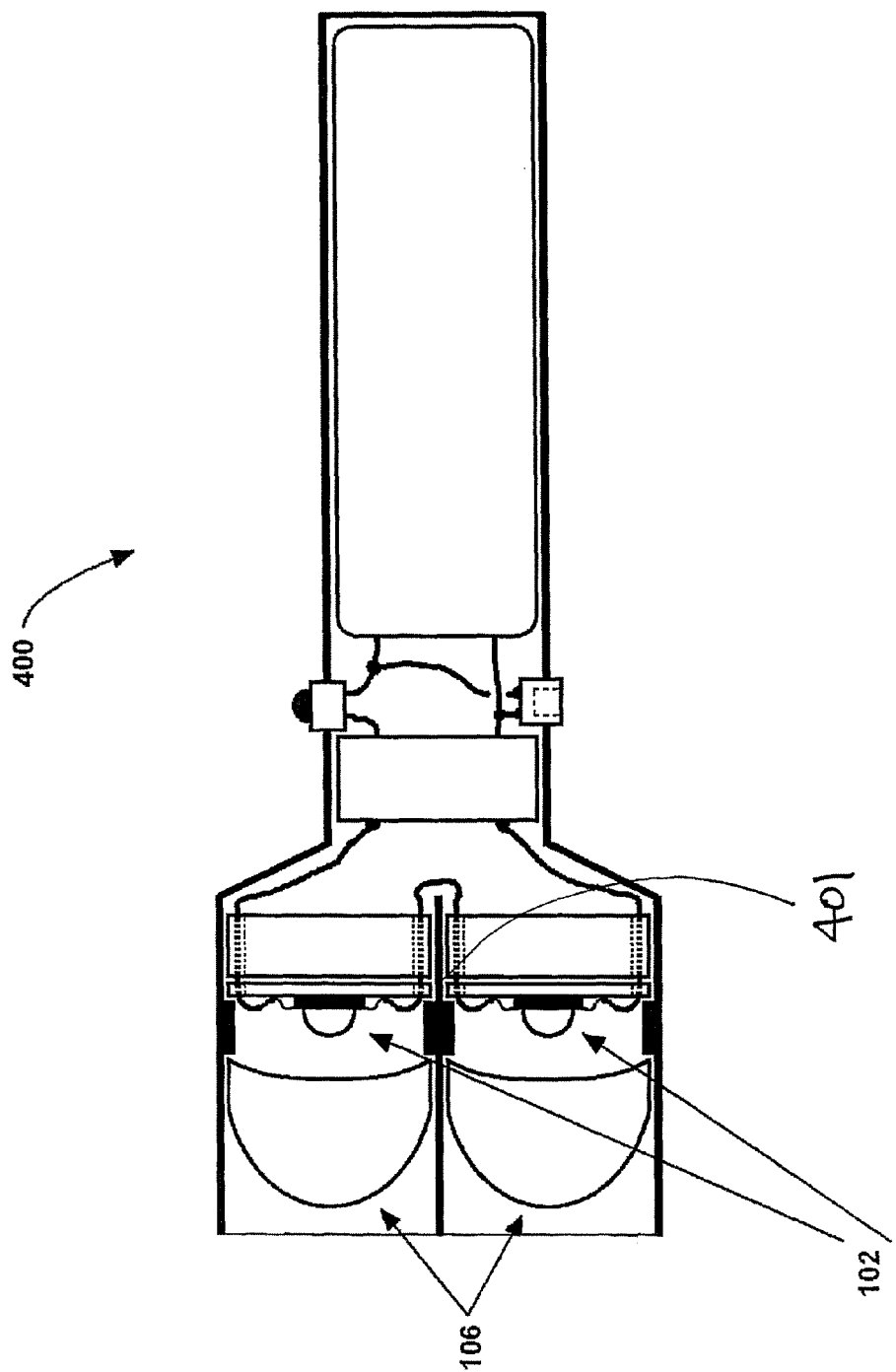
FIG. 4 is a cross sectional side view of a third exemplary embodiment of the present invention.

Referring to FIG. 4, an LED flashlight 400 is shown as resembling the LED flashlight 300 of FIG. 3, except that it has more than one LED 102 and a lens 106 forward of each associated LED 102. Any suitable number of LEDs 102 and individually associated lenses 106 can be used. For example, the number of LEDs 102 and lenses 106 can be seven (one in the center and six surrounding the center one) as that is the maximum ordinarily possible utilizing the specific LEDs described herein, such that the flashlight 400 will have an overall width no more than three times the width that would result from using only one LED 102 and one lens 106. Tubular walls 401 surrounding associated LED 102 and lens 106 combinations in the same manner as the housing 101 of spotlight 100 are preferably provided to block stray light and hold each LED 102 and lens 106 combination in position.

Features of any embodiment described above can be used in other embodiments, including but not limited to other embodiments described above.

Numerous variations from the embodiments described in the above specification are possible, and accordingly the invention is not to be limited to embodiments described above, or to any alternative arrangements and variations described above. More particularly, it will be appreciated by those of ordinary skill in the art that the present invention can be embodied in various specific forms without departing from the spirit or essential characteristics thereof. The presently disclosed embodiments are considered in all respects to be illustrative and not restrictive. The scope of the invention is indicated by the appended claims, rather than the foregoing description, and all changes that come within the meaning and range of equivalence thereof are intended to be embraced.

What is claimed is:

1. An LED spotlight, comprising:
   a) a cylindrical housing,
   b) at least one LED within the housing, each LED having a nominal radiation pattern width of at least about 55 degrees,
   b) means for the at least one LED to receive electrical power, and
   c) at least one circular lens within the housing,
   wherein each lens of the at least one lens is disposed forward of an associated LED of the at least one LED,
   wherein each lens has a diameter of 15 to 26 millimeters, and
   wherein each lens collimates a majority of the light from its associated LED into a beam no more than 10 degrees wide, and all collimation of light by each lens occurs through refraction.

2. The LED spotlight of claim 1 wherein rays of light from each LED are refracted towards an axis of its associated lens upon entering the lens through a rear surface of the lens, and further refracted towards the axis of the lens upon exiting a front surface of the lens.

3. The LED spotlight of claim 1 wherein the lens has a rear surface that is more sharply curved in a concave manner towards its edge than towards its axis.

4. The LED spotlight of claim 1 wherein each LED has an optical center that is located closer to its associated lens than a focal point of the lens.

5. The LED spotlight of claim 1 wherein each LED has an optical center that is located at a focal point of its associated lens.

6. The LED spotlight of claim 1 wherein each LED has a nominal radiation pattern width of at least about 100 degrees.

7. The LED spotlight of claim 6 wherein each LED has a nominal wattage of 1 watt or more.

8. The LED spotlight of claim 6 wherein each LED nominally has a lambertian radiation pattern.

9. The LED spotlight of claim 1 wherein each LED receives power from an external power source.

10. The LED spotlight of claim 1 wherein the housing is metal so as to dissipate heat from each LED.

11. The LED spotlight of claim 10 wherein each LED is mounted to a heatsink plate that conducts heat from the LED to the metal housing.

12. The LED spotlight of claim 1 wherein the distance between each LED of the at least one LED and its associated lens is less than the thickness of the associated lens.

13. The LED spotlight of claim 6 wherein the distance between each LED of the at least one LED and its associated lens is less than the thickness of the lens.

14. The LED spotlight of claim 13 wherein the distance between each LED and its associated lens is less than the distance that would produce a focused beam.

15. The LED spotlight of claim 1 wherein each lens is concavo-convex.

16. The LED spotlight of claim 6 wherein each lens is concavo-convex.

17. The LED spotlight of claim 1 wherein the spotlight is a flashlight.

18. The LED spotlight of claim 17 wherein at least one LED in the flashlight produces light suitable for causing visible fluorescence of fluorescent materials to be detected by use of the flashlight.

19. The LED spotlight of claim 18 wherein the light produced by the at least one LED has a peak wavelength near 365 nanometers.

20. The LED spotlight of claim 18 wherein the light produced by the at least one LED has a peak wavelength near 380 nanometers.

21. The LED spotlight of claim 18 wherein the light produced by the at least one LED has a peak wavelength of about 390 to about 410 nanometers.

22. The LED spotlight of claim 18 wherein the light produced by the at least one LED has a peak wavelength in the blue region of the visible spectrum.

23. The LED spotlight of claim 18 wherein the light produced by the at least one LED has a peak wavelength near 450 nanometers.

24. The LED spotlight of claim 18 wherein the light produced by the at least one LED has a peak wavelength of about 455 to about 475 nanometers.

25. The LED spotlight of claim 1 in combination with headwear.

26. The LED spotlight and headwear combination of claim 25 wherein the headwear is in the shape of an eyeglass frame.

27. The LED spotlight and headwear combination of claim 25 wherein the LED spotlight is integrated with the headwear.

28. The LED spotlight and headwear combination of claim 25 wherein the LED spotlight is mounted to the headwear.

29. The LED spotlight and headwear combination of claim 25 wherein the LED spotlight is detachably mounted to the headwear.

30. The spotlight and headwear combination of claim 29 wherein the combination is suitable for use while performing medical or dental work.

31. The LED spotlight of claim 1 wherein the thickness of each lens at a central axis of the lens exceeds the distance between a rear surface of the lens at the central axis of the lens and its associated LED.

32. The LED spotlight of claim 1 wherein half the thickness of each lens at a central axis of the lens exceeds the distance between a rear surface of the lens at the central axis of the lens and its associated LED.

33. The LED spotlight of claim 1 wherein half the diameter of each lens exceeds the distance between a rear surface of each lens at a central axis of the lens and its associated LED.

34. The LED spotlight of claim 31 wherein the distance between each LED and its associated lens is less than the distance that would produce a focused beam.

35. The LED spotlight of claim 32 wherein the distance between each LED and its associated lens is less than the distance that would produce a focused beam.

36. The LED spotlight of claim 33 wherein the distance between each LED and its associated lens is less than the distance that would produce a focused beam.

37. The LED spotlight of claim 15 wherein a concave rear surface of each concavo-convex lens comprises a convex central portion and a concave outer portion about the central portion.

38. The LED spotlight of claim 1 wherein each LED of the at least one LED has a radiation pattern width of about 55 degrees.

39. An LED spotlight, comprising:
a) a cylindrical housing,
b) at least one LED within the housing, each LED having a nominal radiation pattern width of at least about 55 degrees,
b) means for the at least one LED to receive electrical power, and
c) at least one circular lens within the housing,
wherein each lens has a diameter of 15 to 26 millimeters,
wherein each lens of the at least one lens is disposed forward of an associated LED of the at least one LED,
wherein each lens collimates a majority of the light from its associated LED into a beam no more than about 10 degrees wide, and all collimation of light by each lens occurs through refraction, and
wherein each LED of the at least one LED has a radiation pattern width of at least about 100 degrees.

40. The LED spotlight of claim 39 wherein the spotlight is a flashlight.

41. The LED spotlight of claim 40 wherein at least one LED in the flashlight produces light suitable for causing visible fluorescence of fluorescent materials to be detected by use of the flashlight.

42. The LED spotlight of claim 39 in combination with headwear.

43. The LED spotlight of claim 39 wherein the lens is concavoconvex.

44. The LED spotlight of claim 39 wherein rays of light from each LED are refracted towards an axis of its associated lens upon entering the lens through a rear surface of the lens, and further refracted towards the axis of the lens upon exiting a front surface of the lens.

45. The LED spotlight of claim 39 wherein the lens has a rear surface that is more sharply curved in a concave manner towards its edge than towards its axis.

46. An LED spotlight, comprising:
a) a cylindrical housing,
b) at least one LED within the cylindrical housing, each LED having a nominal radiation pattern width of at least about 55 degrees, b) means for the at least one LED to receive electrical power, and
c) at least one lens within the housing,
wherein each lens of the at least one lens is disposed forward of an associated LED of the at least one LED,
wherein each lens has a diameter of about 15 to about 26 millimeters,
wherein each lens is concavoconvex,
wherein each lens has its rear surface more sharply curved in a concave manner towards its edge than towards its axis,
wherein the distance between each lens and its associated LED is less than the thickness of the lens, and
wherein each lens collimates light from the lens into a beam that has a width of no more than about 10 degrees, and all collimation of light by each lens occurs through refraction.

47. An LED spotlight, comprising:
a) a cylindrical housing,
b) at least one LED within the housing, each LED having a nominal radiation pattern width of at least about 55 degrees,
b) means for the at least one LED to receive electrical power, and
c) at least one lens within the housing,
wherein each lens has a diameter of about 15 to about 26 millimeters,
wherein each lens of the at least one lens is disposed forward of an associated LED of the at least one LED,
wherein each lens collimates a majority of the light from its associated LED into a beam no more than about 10 degrees wide, and all collimation of light by each lens occurs through refraction, and
wherein each LED of the at least one LED has a radiation pattern width of about 55 degrees,
wherein each LED has a power rating of at least 1 watt, and
wherein each LED produces light of wavelengths suitable for causing visible fluorescence of fluorescent materials.

* * * * *